US006818393B1

(12) United States Patent
Mach et al.

(10) Patent No.: US 6,818,393 B1
(45) Date of Patent: Nov. 16, 2004

(54) DNA SEQUENCES CODING FOR THE DR BETA-CHAIN LOCUS OF THE HUMAN LYMPHOCYTE ANTIGEN COMPLEX AND POLYPEPTIDES, DIAGNOSTIC TYPING PROCESSES AND PRODUCTS RELATED THERETO

(75) Inventors: Bernard Francois Mach, Geneva (CH); Eric Olivier Long, Chevy Chase, MD (US); Claire Terese Wake, Somerville, MA (US)

(73) Assignee: bioMirieux sa, Marcy l'Etoile (FR)

( * ) Notice: Subject to any disclaimer, the term of this patent is extended or adjusted under 35 U.S.C. 154(b) by 0 days.

(21) Appl. No.: 08/484,786

(22) Filed: Jun. 7, 1995

Related U.S. Application Data

(62) Division of application No. 07/902,999, filed on Jun. 23, 1992, now Pat. No. 5,503,976, which is a division of application No. 06/518,393, filed on Jul. 29, 1983, now Pat. No. 5,169,941.

(30) Foreign Application Priority Data

Jul. 30, 1982 (GB) .......................................... 8 222 066
Oct. 25, 1982 (GB) .......................................... 8 230 441

(51) Int. Cl.[7] .......................... C12Q 1/68; C12P 19/34; C07H 21/04
(52) U.S. Cl. ........................ 435/6; 435/91.1; 536/23.1; 536/24.3
(58) Field of Search ...................... 435/6, 91.1, 91.2; 536/23.1, 24.3, 24.33; 437/7.1–7.9

(56) References Cited

U.S. PATENT DOCUMENTS

| | | | |
|---|---|---|---|
| 4,394,443 A | 7/1983 | Weissman et al. ............. | 435/6 |
| 4,478,823 A | 10/1984 | Sanderson .................... | 424/88 |
| 4,582,788 A | 4/1986 | Erlich ............................ | 435/6 |
| 5,110,920 A | 5/1992 | Erlich .......................... | 536/24 |
| 5,169,941 A | * 12/1992 | Mach et al. .................. | 536/27 |
| 5,310,893 A | 5/1994 | Erlich et al. ............. | 536/24.31 |
| 5,468,613 A | 11/1995 | Erlich et al. .................. | 435/6 |
| 5,503,976 A | 4/1996 | Mach et al. .................. | 435/6 |
| 5,541,065 A | 7/1996 | Erlich et al. .................. | 435/6 |

FOREIGN PATENT DOCUMENTS

| | | | | |
|---|---|---|---|---|
| EP | 54676 | 6/1982 | ............ | C12Q/1/66 |
| EP | 84796 | 8/1983 | ............ | C12N/15/00 |
| GB | 2019408 A | 10/1979 | ............ | C07H/21/00 |
| WO | WO 80/01986 | 10/1980 | ............ | A61K/39/00 |
| WO | WO 82/02060 | 6/1982 | ............ | C12Q/1/68 |
| WO | WO 83/03260 | 9/1983 | ............ | C12Q/1/68 |
| WO | WO 92/10589 | 6/1992 | ............ | C12Q/1/68 |
| WO | WO 92/11389 | 7/1992 | ............ | C12Q/1/68 |

OTHER PUBLICATIONS

Wallace et al. Methods in Enzymologym vol. 152; 432–443, 1987.*

(List continued on next page.)

*Primary Examiner*—Jehanne Sitton
(74) *Attorney, Agent, or Firm*—Fish & Neave; James F. Haley, Jr.; Margaret A. Pierri

(57) ABSTRACT

DNA sequences coding for the DR-β-chain locus of human lymphocyte antigen complex and diagnostic typing processes and products related thereto. DNA sequences that code for the β-chain DR locus are useful in simple and efficient typing processes and products and for expression of polypeptides displaying an immunological or biological activity of the antigens of the HLA-DR β-chains for use in diagnostic, preventive and therapeutic agents.

5 Claims, 16 Drawing Sheets

OTHER PUBLICATIONS

Sambrook et al. In Molecular Cloning a LAb manual psage 11.47, 1987.*

Larhammer et al. Proc. Natl. Acad. Sci vol. 79, pp. 3687–3691, Jun. 1982.*

Kratzin, H. et al., Primary Structure of Human Histocompatibility Antigens of Class II, "Part I: Amino Acid Sequence of the N–terminal 198 Radicals of the β–chain of HLA–Dw2,2;DR2,2–Alloantigens," *Hoppe–Seyler's Z. Physiol. Chem.* 362:1665–1669 (1981). (Copies of the original version, in German, along with an English–language translation, are enclosed.).

Abaza, M. I. et al., "Effects of Amino Acid Substitutions Outside an Antigenic Site on Protein Binding to Monoclonal Antibodies of Predetermined Specificity Obtained by Peptide Immunization: Demonstration with Region 94–100 (Antigenic Site3) of Myoglobin", *Journal of Protein Chemistry*, 11:433–444 (1992).

Dresser, D.W., *Chapter 8: Immunization of experimental animals*, in *Handbook of Experimental Immunology in Four Volumes—vol. 1: Immunochemistry*, Eds. Weir, D.M., Herzenberg, L.A., Blackwell, C. and Herzenberg, L.A., 4th edition, pp. 8.14–8.15 (1986).

William, A.F. and Barclay, A.N., *Chapter 22: Glycoprotein antigens of the lymphocyte surface and their purification by antibody affinity chromatography*, in *Handbook of Experimental Immunology in Four Volumes—vol. 1: Immunochemistry*, Eds. Weir, D.M., Herzenberg, L.A., Blackwell, C. and Herzenberg, L.A., 4th edition, pp. 22.14–22.15 (1986).

L.A. Lampson and R. Levy, "Two Populations of Ia–Like Molecules on a Human B Cell Line", *J. Immunol.*, 125, pp. 293–299 (1980).

Dognin M. J. et al. "Multiple amino acid substitutions between murine y2a heavy chain Fc regions of Igla and Iglb allotypic forms" *Proceedings of the National Academy of Science USA* 78, 4031–4035 (1981).

Carrell S. et al. "Subsets of Human Ia–Like Molecules defined by Monoclonal Anitbodies" *Molecular Immunology* 18(5) 403–411 (1981).

Accolla R.S. et al. "Demonstration at the Single–cell level of existence of distinct clusters of epitopes in two predefined human Ia molecular subsets" *European J. Immunology* 12, 166–169 (1982).

R. S. Accolla et al., *Proc. Natl. Acad. Sci. USA*, 78, pp. 4549–4551 (1981).

R. H. Bach et al., *N. Engl. J. Med.*, 295, pp. 806–813 (1976).

B. Benacerraf in *The Role Of The Major Histocompatibility Complex In Immunobiology*, M. Dorf, ed., Garland Publishing, pp. 255–269 (1981).

J. Bohme et al., "Human Class II Major Histocompatibility Antigen β–chains are Derived From at least Three Loci", *Nature*, 301, pp. 82–84 (1983).

R. Bono et al., *Nature*, 299, pp. 836–838 (1982).

B. Cami et al., "Multiple Sequences Related to Classical Histocompatibility Antigens In the Mouse Genome", *Nature*, 291, pp. 673–675 (1981).

S. Carrel et al., *Mol. Immunol.*, 18, pp. 403–411 (1981)l

D. J. Charron et al., *J. Exp. Med.*, 152, pp. 18s–36s (1980).

G. Corte et al., *Proc. Natl. Acad. Sci. USA*, 78, pp. 534–538 (1981) [Corte I].

G. Corte et al., *Nature*, 292, pp. 357–360 (1981) [Corte II].

O. Finn et al., "Multiple HLA–DR Antigens: Detection With Monoclonal Antibodies And Tanslation In Vitro", *Proc. Natl. Acad. Sci. USA*, 79, pp. 2658–2662 (Apr. 1982).

S. M. Goyert et al., *J. Exp. Med.*, 156, pp. 550–566 (Aug. 1982).

Gustafsson et al., "Mutations and Selection in the Generation of Class II Histocompatibility Antigen Polymorphism", *EMBO J*, 3, pp. 1655–1661 (1984).

Itakura et al., "Expression in E.coli of a Gene Chemically Synthesized for the Hormone Somatostatin", *Science*, 198, pp. 1056–1063 (1977).

Y. Kajimura et al., "Entire Amino Acid Sequence Of HLA–DR Beta Chain Deduced From The Cloned Complementary DNA Sequence", *J. Cell Biol.*, 95, p. 217A (Nov. 1982) [Biol. Abstracts 95:25070862].

H. Kratzin et al., *Hoppe Seyler's Z. Physiol. Chem.*, 362, pp. 1665–1669 (1981).

S. Kvist et al., "cDNA Clone Coding For Part Of A Mouse $H-2^d$ Major Histocompatibility Antigen", *Proc. Natl. Acad. Sci. USA*, 78, pp. 2772–2776 (1981).

D. Larhammar et al., "Complete Amino Acid Sequence Of An HLA–DR Antigen–Like βChain As Predicted From the Nucleotide Sequence: Similarities with Immunoglobulins and HLA–A, –B and –C Antingens", *Proc. Natl. Acad. Sci. USA*, 79, pp. 2687–2691 (Jun. 1982).

E. Long et al., "Molecular Cloning of HLA–DR Antigen cDNA Fragments", *Experimentia*, 38, p. 744 (1982) [Long I].

E. Long et al., "Isolation Of Distinct cDNA Clones Encoding HLA–DR Chains By Use of An Expression Assay", *Proc. Natl. Acad. Sci. USA*, 79, pp. 7465–7469 (Dec. 1982) [Long II].

E. Long et al., "Translation And Assembly Of HLA–DR Antigens In Xenopus Oocytes Injected With mRNA From A Human B–Cell Line", *EMBO J.*, 1(5), p. 649–54 (Oct. 11, 1982) [Chem. Abstracts 97:125456n] [Long III].

Nadler et al., *Nature*, 290, pp. 591–593 (1981).

D. Owerbach et al., "Detection Of HLA–D/DR–Related DNA Polymorphism In HLA–D Homozygous Typing Cells", *Proc. Natl. Acad. Sci. USA*, 80, pp. 3758–1961 (Jun. 1983).

Ploegh et al., "Molecular Cloning Of A Human Histocompatibility Antigen cDNA Fragment", *Proc. Natl. Acad. Sci. USA*, 77, pp. 6081–6085 (Oct. 1980).

V. Quaranta et al., *J. Immunol.*, 125, p. 1421–25 (1980).

L. P. Ryder et al., "Genetics Of HLA Disease Association", *Ann. Rev. Genet.*, 15, pp. 169–187 (1981).

T. Sasazuki et al., "The Association Between Genes In The Major Histocompatibility Complex And Disease Susceptibility", *Ann. Rev. Med.*, 28, pp. 425–452 (1977).

D. A. Shackelford et al., *Proc. Natl. Acad. Sci. U.S.A.*, 78, pp. 4566–4570 (1981) [Shackelford I].

D. A. Shackelford et al., *Immunol. Rev.*, 66, pp. 133–187 (1982) [Shackelford II].

S. Shaw et al., *J. Exp. Med.*, 156, pp. 731–743 (Sep. 1982).

A. Sood et al., "Isolation And Partial Nucleotide Sequence Of a cDNA Clone For Human Histocompatibility Antigen HLA–B By Use Of An Oligodeoxynucleotide Primer", *Proc. Natl. Acad. Sci. USA*, 78, pp. 616–620 (1981).

J. L. Strominger et al., in *The Role Of The Major Histocompatibility Complex In Immunobiology*, M. Dorf, ed., Garland Publishing, pp. 115–172 (1981).

R. Tosi et al., *J. Exp. Med.*, 148, pp. 1592–1611 (1978).

Y. Wai Kan et al., "Polymorphism Of DNA Sequences Adjacent To Human–globin Structural Gene: Relationship To Sickle Mutation", *Proc. Natl. Acad. Sci. USA*, 75, pp. 5631–5635 (1978).

K. Wiman et al., "Isolation and Identification Of A cDNA Clone Corresponding To An HLA–DR Antigen Beta Chain", *Proc. Natl. Acad. Sci. USA*, 79, pp. 1703–1707 (Mar. 1982).

* cited by examiner

Raji Cells
↓ extraction
Poly A+ RNA
↓ Size fractionation
HLA-DR β-chain Poly A+ RNA
+
other RNAs
↓ (1) reverse transcriptase
  (2) double stranding
HLA-DR β-chain cDNA (ds)
+
other cDNA (ds)'s
↓ (1) dC-tailing
  (2) Ligation
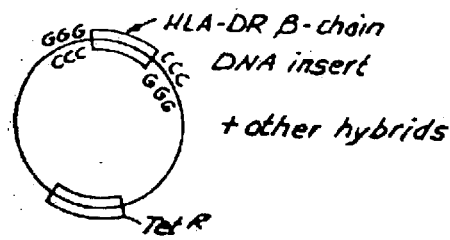
HLA-DR β-chain DNA insert
+ other hybrids
↓ (1) Transfection
  (2) screening
  (3) Excision
HLA-DR β-chain cDNA inserts
FIG. 2
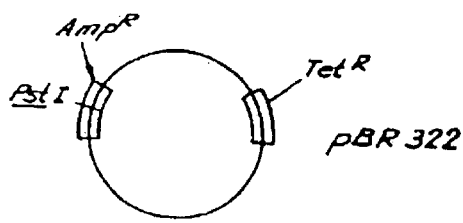
pBR 322
(1) Pst I
(2) dG-tailing
made competant → E. coli: HB101

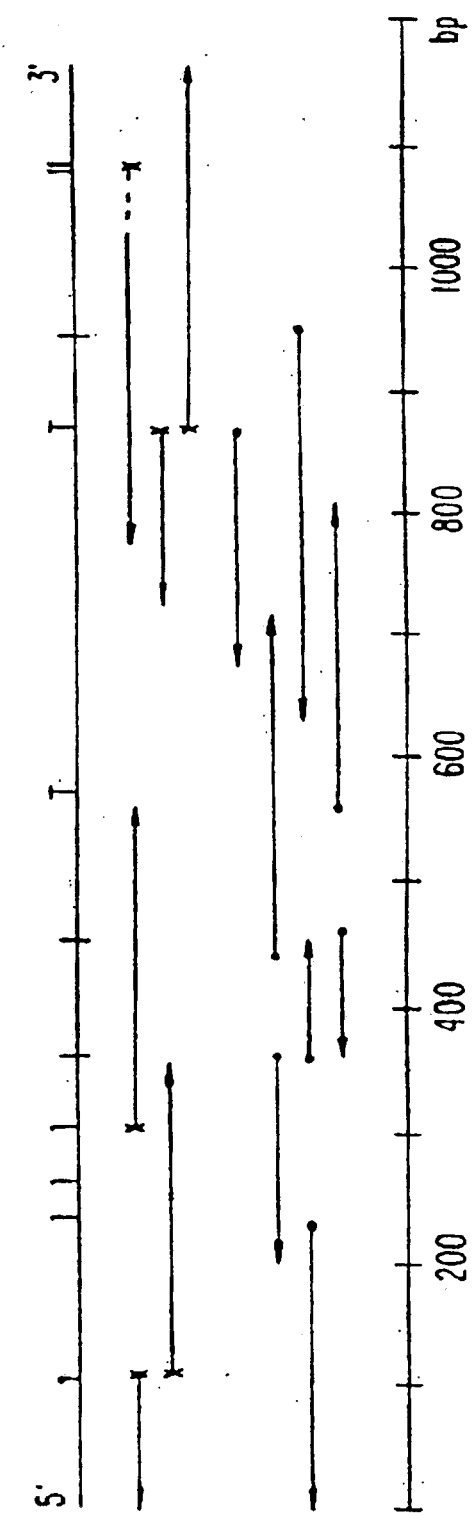

```
                                                      -29
                                                       M    V    C    L
(G)n CTCCTCTGGCCCCCTGGTCCTGTCCTCTCTTCTCCAGC           ATG  GTG  TGT  CTG    47

K    L    P    G    G    S    S    L    A    A    L    T    V    T
     AAG  CTC  CCT  GGA  GGC  TCC  AGC  TTG  GCA  GCG  TTG  ACA  GTG  ACA   89

1
     L    M    V    L    S    R    L    A    F    A    G    D    T
     CTG  ATG  GTG  CTG  AGC  TCC  CGA  CTG  GCT  TTC  GCT  GGG  GAC  ACC   131

10
     R    P    R    F    L    E    L    L    K    S    E    C    H    F
     CGA  CCA  CGT  TTC  TTG  GAG  CTG  CTT  AAG  TCT  GAG  TGT  CAT  TTC   173

20                                           30
     F    N    G    T    E    R    V    R    R    F    L    E    R    F
     TTC  AAT  GGG  ACG  GAG  CGG  GTG  CGG  CGG  TTC  CTG  GAG  AGA  TTC   215

40
     H    N    Q    E    E    Y    A    R    F    D    S    D    V    G
     CAT  AAC  CAG  GAG  GAG  TAC  GCG  CGC  TTC  GAC  AGC  GAC  GTG  GGG   257

FIG. 5B
```

```
 E   Y   R   A   V   R   E   L   G   R   P   D   A   E
             50
GAG TAC CGG GCG GTG AGG GAG CTG GGG CGG CCT GAT GCC GAG      299

Y   W   N   S   Q   K   D   L   L   E   Q   K   R   G
60                                  70
TAC TGG AAC AGC CAG AAG GAC CTC CTG GAG CAG AAG CGG GGC      341

Q   V   D   N   Y   C   R   H   N   Y   G   V   V   E
                80
CAG GTG GAC AAT TAC TGC AGA CAC AAC TAC GGG GTT GTG GAG      383

S   F   T   V   Q   R   R   V   H   P   Q   V   T   V
         90                                     100
AGC TTC ACA GTG CAG CGG CGA GTC CAT CCT CAG GTG ACT GTG      425

Y   P   A   K   T   Q   P   L   Q   H   H   N   L   L
                                110
TAT CCT GCA AAG ACC CAG CCC CTG CAG CAC CAC AAC CTC CTG      467

V   C   S   V   S   G   F   Y   P   G   S   I   E   V
             120
GTC TGC TCT GTG AGT GGT TTC TAT CCA GGC AGC ATT GAA GTC      509
```

FIG. 5C

```
130   R   W   F   R   N   G   Q   E   E   K   A   G   V   V
      AGG TGG TTC CGG AAC GGC CAG GAG GAA AAG GCT GGG GTG GTG    551
                                         140

S   T   G   L   I   Q   N   G   D   W   T   F   Q   T
      TCC ACG GGC CTG ATC CAG AAT GGA GAC TGG ACC TTC CAG ACC    593
                      150

L   V   M   L   E   T   F   P   R   S   G   E   V   Y
      CTG GTG ATG CTA GAA ACA TTT CCT CGG AGT GGA GAG GTT TAC    635
              160                                 170

T   C   Q   V   E   H   P   S   V   T   S   P   L   T
      ACC TGC CAA GTG GAG CAC CCA AGC GTA ACG AGC CCT CTC ACA    677
                                     180

V   E   W   S   A   R   S   E   S   A   Q   S   K   M
      GTG GAA TGG AGT GCA CGG TCT GAA TCT GCA CAG AGC AAG ATG    719
                      190

L   S   G   V   G   G   F   V   L   G   L   L   F   L
      CTG AGT GGA GTC GGG GGC TTT GTG CTG GGC CTG CTC TTC CTT    761
      200                                 210
```

FIG. 5D

```
               220
      G   L   F   I   Y   F   R   N   Q   K   G   H
G   A   G   L   F   I   Y   F   R   N   Q   K   G   H
GGG GCC GGG CTG TTC ATC TAC TTC AGG AAT CAG AAA GGA CAC      803
              230                 237
      G   L   Q   P   T   G   F   L   S
S   G   L   Q   P   T   G   F   L   S
TCT GGA CTT CAG CCA ACA GGA TTC CTG AGC TGA AGTGCAGATGA      847

CAATTTAAGGAAGAATCTTCTCCCCAGCTTTGCAGGATGAAAAGCTTTCCCGCC       902

TGGCTGTGTTATTCTTCCACGAGAGAGGGCTTTCTCAGGACCTAGTTGCTACTGGTT    957

CAGCAACTGCAGAAAATGTCCTCCCTTGTGGCTTCCTCAGTTCCTGCCCTTGGCC     1012

TGAAGTCCCAGCATTGATGGCAGCGCCTCATCTTCAACTTTTGTGCTCCCCTTTG     1067

CCTAAACCCTATGGCCCTGTGTACTCACCCTGTACCACAAACACATT             1122

ACATTATTAAATGTTTCTCAAAGATGGAGTTAAAAAAAA(C)n                 1160
```

FIG. 5E

```
DR4,6   GQTRPRFLELLKSECHFFNGTERVRFLERHFHNQEEYARFDSDVGEYRAVRELGRPDAEYWNSQKDLLEQKRGQVCNYC

DR2,2   -------WQP-R---------O-Y-Y----SV-------F----T-------------I---A-AA--T--

DC      R-SPED-VYQF-GM-Y-T-----LVS-SIY-R--VV-------F----TL--L-A-------I--R--AA--RV-
```

FIG. 6A

```
                    80                          100
                     •                           •
DR4,6    RHNYGVVESFTVQRRVHPQVTVYPAKTQPLQHHNLLV
DR2,2    ------------Q-K----S------------------
DC       ----QLELRT-L----E-T---IS--SR-EA-N-----
```

FIG. 6B

```
              180                    200                    220
DR4,6   QVEHPSVTSPLTVEWSARSESAQSKM|LSGVGGFVLGLLFLGAGLFIYF|RNQKGHSGLQPTGFLS

DR2,2   ------------------R-------|---------------------|----------------

DC      H----LQ--I----R-Q---------|---I------I---L--I-HH|-S----LLH
```

```
                                                            M   V   C   C   L   K   F   P   G
  A GTT CTC CCT GAG TGA GAC TCA CCT GCT CCT CTG GCC CCT GTC CTG TTC TCC AGC ATG GTG TGT TGT CTG AAG TTC CCT GGA    85

-1  1
 G   S   C   M   A   A   L   I   V   T   M   V   L   S   A   G   D   T   R   P   R   F   L
GGC TCC TGC ATG GCA GCT CTG ACA GTG ATG GTG CTG AGC TCC CCA GCT TTG GCT GGG GAC ACC CGA CCA CGT TTC TTG           172

30
 E   V   K   H   C   H   F   N   E   R   V   F   L   D   R   Y   F   H   Q   E   E   Y   T
GAG GTT AAA CAT TGT CAT TTC AAC GAG CGG GTG TTC CTG GAC AGA TAC TTC CAT CAA GAG GAG TAC                            259

60
 V   R   F   D   S   D   V   G   V   Y   R   A   E   P   D   A   E   Y   W   N   S   Q   D
GTG CGC TTC GAC AGC GAC GTG GGG GAG TAC CGG GCG GAG CCT GAT GCC GAG TAC TGG AAC AGC CAG GAC                         346

90
 L   L   E   Q   K   R   A   A   V   D   T   Y   C   R   H   N   Y   G   V   G   E   S   F   T   V   Q   R   R   V
CTC CTG GAG CAG AAG CGG GCC GCG GTG GAC ACC TAC TGC AGA CAC AAC TAC GGG GTT GGT GAG AGC TTC ACA GTG CAG CGG CGA GTC 433

120
 Y   P   E   V   T   V   Y   P   A   K   T   Q   P   L   Q   H   H   N   L   L   V   C   S   V   N   G   F   Y   P
TAT CCT GAG GTG ACT GTG TAT CCT GCA AAG ACC CAG CCC CTG CAG CAC CAC AAC CTC CTG GTC TGC TCT GTG AAT GGT TTC TAT CCA 520

150
 G   S   I   E   V   R   W   F   R   N   G   Q   E   E   K   A   G   V   V   S   T   G   L   I   Q   N   G   D   W
GGC AGC ATT GAA GTC AGG TGG TTC CGG AAC GGC CAG GAA GAG AAG ACT GGG GTG GTG TCC ACA GGC CTG ATC CAG AAT GGA GAC TGG 607
```

FIG. 7A

```
           I   F   Q   T   G   V   M   I   E   T   V   P   R   S   G   E      Y   T   C   Q   V   E   H   P   S   L   T   S
          160                     170                     180
ACC TTC CAG ACC CTG GTG ATG CTG GAA ACA GTT CCT CGG AGT GGA GAG GTT TAC ACC TGC CAA GTG GAG CAC CCA AGC CTG ACG AGC   694
                 190                                         200                                            210
    P   L   L   V   E   W   R   A   R   S   E       S   A   Q   S   K   M   M   S   L   S   G   V   G   F   V   G   L   L
CCT CTC ACA GTG GAA TGG AGA GCA CGG TCT GAA TCT GCA CAG AGC AAG ATG AGT CTG AGT GGA GTC GGG GGC TTC GTG GGC CTG CTC   781
    F   L   G   A   G   L   F   I   Y   F   R   N   Q   K       G       Q   P   T   Q   G   F   L   Q
                                 220                             230            237
TTC CTT GGG GCC GGG CTG TTC ATC TAC TTG AGG AAT CAG AAA GGA CAC TCT GGA CTC CAG CCA ACA GGA TTC CTG AGC TGA AGT GAA   868

GAT GAC CAC ATT CAA GGA AGA ACC TTC TGC CCC AGC TTT GCA GGA TGA AAC ACT TCC CCG CTT GGC TCT CAT TCT TCC ACA AGA GAG   955

ACC TTT CTC CGG ACC TGG TTG CTA CTG GTT CAG CAG CTC TGC AGA AAA TGT CCT CCC TTG TGG CTG CCT CAG CTC GTA CCT TTG GCC  1042

TGA AGT CCC AGC ATT AAT GGC AGC CCC TCA TCT TCC AAG TTT TGT GCT CCC CTT TAC CTA ATG CTT CCT GCG TCC CAT GCA TCT GTA  1129

CTC CTG CTG TGC CAC AAA CAC ATT ACA TTA TTA AAT GTT TCT CAA ACA TGG AGT TAA AAA AAA AAA AAA AAA AAA AAA AAA AAA AA   1215
```

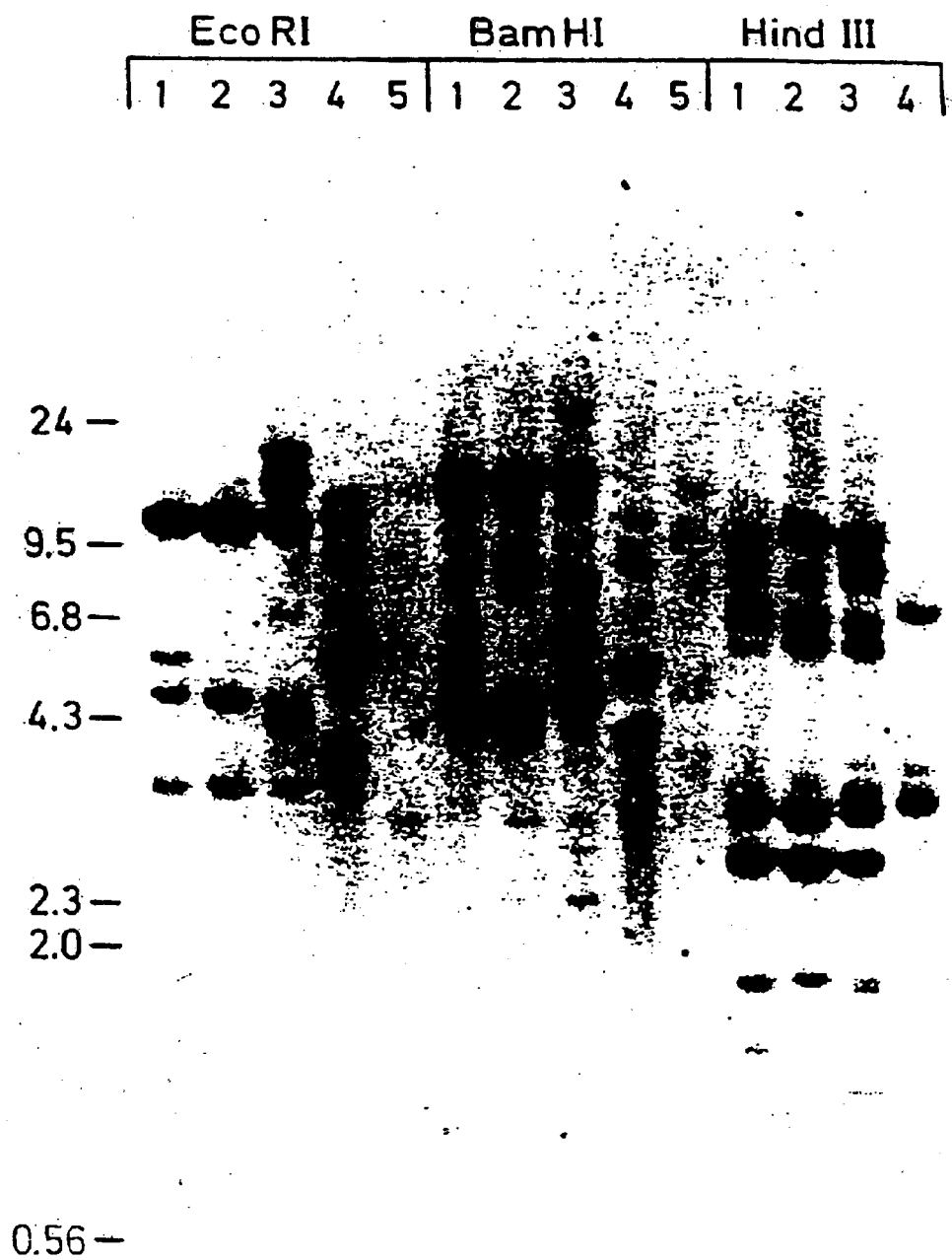

FIG. 9

Region I

| AA | 8 | 9 | 10 | 11 | 12 | 13 | 14 |
|---|---|---|---|---|---|---|---|
|  | L | E | L | L | K | S | E |
| HLA-DR-β-A | TTG | GAG | CTG | CTT | AAG | TCT | GAG |
| HLA-DR-β- | TTG | GAG | CAG | GTT | AAA | CAT | GAG |
|  | L | E | Q | V | K | H | E |

Region II

| AA | 26 | 27 | 28 | 29 | 30 | 31 | 32 |
|---|---|---|---|---|---|---|---|
|  | F | L | E | R | H | F | H |
| HLA-DR-β-A | TTC | CTG | GAG | AGA | CAC | TTC | CAT |
| HLA-DR-β- | TTC | CTG | GAC | AGA | TAC | TTC | TAT |
|  | F | L | D | R | Y | F | Y |

Region III

| AA | 72 | 73 | 74 | 75 | 76 | 77 | 78 |
|---|---|---|---|---|---|---|---|
|  | R | G | Q | V | D | N | Y |
| HLA-DR-β-A | CGG | GGC | CAG | GTG | GAC | AAT | TAC |
| HLA-DR-β- | CGG | GCC | GCG | GTG | GAC | ACC | TAC |
|  | R | A | A | V | D | T | Y |

DNA SEQUENCES CODING FOR THE DR BETA-CHAIN LOCUS OF THE HUMAN LYMPHOCYTE ANTIGEN COMPLEX AND POLYPEPTIDES, DIAGNOSTIC TYPING PROCESSES AND PRODUCTS RELATED THERETO

This is a divisional of application Ser. No. 07/902,999, filed Jun. 23, 1992, now U.S. Pat. No. 5,503,976, which is a division of application Ser. No. 06/518,393, filed Jul. 29, 1983, now U.S. Pat. No. 5,169,941.

TECHNICAL FIELD OF THE INVENTION

This invention relates to DNA sequences that code for the DR β-chain locus of the human lymphocyte antigen complex. More particularly, it relates to the use of those DNA sequences in diagnostic typing processes and products. Such processes and products are useful in determining an individual's susceptibility to a wide variety of diseases and an individual's characteristics as a donor or acceptor of a tissue or organ transplant. The DNA sequences of this invention are also useful in the expression of polypeptides encoded by them.

BACKGROUND ART

The human lymphocyte antigen ("HLA") system is the major histocompatibility complex in man. It, therefore, constitutes the strongest barrier for tissue and organ transplants between individuals, apparently distinguishing between self and non-self. In addition, HLA factors have been demonstrated to be associated with increased susceptibility to a wide variety of diseases. Therefore, the antigens of the HLA system have found use in diagnostic typing processes and products for determining an individual's susceptibility to a wide variety of diseases and his characteristics as a donor or acceptor of a tissue or organ transplant [F. H. Bach and J. J. Van Rood, *N. Engl. J. Med.*, 295, pp. 806–13 (1976)].

From a genetic point of view the HLA system is fairly well characterized. See e.g., L. P. Ryder et al., "Genetics Of HLA Disease Association", *Ann. Rev. Genet.*, 15, pp. 169–87 (1981); J. L. Strominger et al., in *The Role of the Major Histocompatibility Complex in Immunobiology*, M. Dorf, ed., Garland SPTM Press, pp. 115–172 (1981); T. Sasazuki et al., "The Association Between Genes In The Major Histocompatibility Complex And Disease Susceptibility", *Ann. Rev. Med.*, 28, pp. 425–52 (1977). It consists of a series of more or less highly polymorphic loci situated within an interval of about 2 centimorgan (cM) on the short arm of chromosome 6. Three loci in that system (HLA-A, B and C) encode one class of codominantly expressed alloantigens (Class 1). Another locus (HLA-D/DR) encodes a second class of codominant alloantigens with a high degree of recognized polymorphism (Class 2). Three other loci, controlling some of the initial components (C2, C4 and factor Bf) of the complement cascade, also belong to the HLA system (Class 3). Finally, there is an non-specific region in the HLA complex designated Ia. Region Ia appears related to, but different than, the DR locus.

The biology of the HLA system is less well understood. Class 1 factors are distributed in all tissues except erythrocytes. Class 2 factors are substantially restricted to β-lymphocytes and mononuclear phagocytic cells and the Class 3 complement factors are directly involved in the activation of the C3 factor, key component in the complement system. The HLA-DR antigens appear to be involved in immunological phenomena—immune responsiveness, T-cell suppression, T-cell and β-cell cooperation and T-cell and macrophage presentation [B. Benacerraf in "The Role Of The Major Histocompatibility Complex In Immunobiology", M. E. Dorf, ed., Garland SPTM Press, pp. 255–69 (1981)].

The HLA-DR antigens are composed of two non-covalently-linked glycosylated peptide chains, a heavy or α-chain of about 35000 molecular weight and a light or β-chain of about 29000 molecular weight, that span the cellular membrane [Strominger et al., supra; and Ryder et al., supra]. Intracellularly, a third peptide chain of about 32000 molecular weight is associated with the α- and β-chains [D. J. Charron and H. O. McDevitt, *J. Exp. Med.*, 152, pp. 180–365 (1980); Strominger, supra]. It appears that the light or β-chain carries the polymorphism of the HLA-DR antigens, while the α-chain and third chain appear identical in different individuals [G. Corte et al., *Proc. Natl. Acad. Sci. USA*, 78, pp. 534–38 (1981); Charron and McDevitt, supra]. Several serologically distinct HLA-DR antigens have been identified—HLA-DR1 through HLA-DR8—and monoclonal antibodies have defined subparts of DR antigens within homozygous cell lines [V. Quaranta et al., *J. Immunol.*, 125, pp. 1421–25 (1980); S. Carrel et al., *Mol. Immunol.*, 18, pp. 403–11 (1981)]. At least two DR β-chains can also be distinguished in several homozygous cell lines by peptide analysis [R. S. Accolla et al., *Proc. Natl. Acad. Sci. USA*, 78, pp. 4549–51 (1981)].

Several other loci also exist that encode polymorphic Ia-like antigens that are closely linked but not identical, to HLA-DR [G. Corte et al., *Nature*, 292, pp. 357–60 (1981); Nadler et al., *Nature*, 290, pp. 591–93 (1981)]. These distinct subregions are called DC [R. Tosi et al., *J. Exp. Med.*, 148, pp. 1592–1611 (1978); D. A. Shackelford et al., *Proc. Natl. Acad. Sci. USA*, 78, pp. 4566–70 (1981)] and SB [S. Shaw et al., *J. Exp. Med.*, 156, pp. 731–43 (1982)]. The DC antigens are in strong linkage disequilibrium with the DR antigens. SB antigens control a secondary lymphocyte reaction and are encoded in a region centromeric to the DR loci.

At present the HLA-DR antigens are isolated serologically by precipitation with antisera. Therefore, the exact nature of the HLA-DR determinants is uncertain. However, these antigens have found use in typing processes and products to determine the compatibility of donors and acceptors for tissue or organ transplants and to determine susceptibility of an individual to a wide variety of diseases. For example, Ryder et al., supra, has reported the following disease susceptibilities based on DR1 through DR8 typing:

| Disease | Typing | Postive Frequency (%) | | Relative Risk | Ethiologica Fraction |
|---|---|---|---|---|---|
| | | Patients | Controls | | |
| Dermatitis herpetiformis | D/DR3 | 85 | 26.3 | 15.4 | 0.80 |
| Coeliac disease | D/DR3 | 79 | 26.3 | 10.8 | 0.72 |
| | D/DR7 also increased | | | | |
| Sicca syndrome | D/DR3 | 78 | 26.3 | 9.7 | 0.70 |
| Idiopathic Addison's disease | D/DR3 | 69 | 26.3 | 6.3 | 0.58 |
| Graves' disease | D/DR3 | 56 | 26.3 | 3.7 | 0.42 |
| Insulin-dependent diabetes | D/DR3 | 56 | 28.2 | 3.3 | 0.39 |
| | D/DR4 | 75 | 32.2 | 6.4 | 0.63 |
| | D/DR2 | 10 | 30.5 | 0.2 | — |
| Myasthenia gravis | D/DR3 | 50 | 28.2 | 2.5 | 0.30 |
| | B8 | 47 | 24.6 | 2.7 | 0.30 |
| SLE | D/DR3 | 70 | 28.2 | 5.8 | 0.58 |
| Idiopathic membraneous nephropathy | D/DR3 | 75 | 20.0 | 12.0 | 0.69 |
| Multiple sclerosis | D/DR2 | 59 | 25.8 | 4.1 | 0.45 |
| Optic neuritis | D/DR2 | 46 | 25.8 | 2.4 | 0.27 |
| Goodpasture's syndrome | D/DR2 | 88 | 32.0 | 15.9 | 0.82 |
| Rheumatoid arthritis | D/DR4 | 50 | 19.4 | 4.2 | 0.38 |
| Pemphigus | D/DR4 | 87 | 32.1 | 14.4 | 0.81 |
| IgA nephropathy | D/DR4 | 49 | 19.5 | 4.0 | 0.37 |
| Hydralazine-induced SLE | D/DR4 | 73 | 32.7 | 5.6 | 0.60 |
| Hashimoto's thryoiditis | D/DR5 | 19 | 6.9 | 3.2 | 0.13 |
| Pernicious anemia | D/DR5 | 25 | 5.8 | 5.4 | 0.20 |
| Juvenile rheumatoid arthritis: pauciart | D/DR5 | 50 | 16.2 | 5.2 | 0.40 |

From these typings, it can be seen that an individual typed positive for D/DR4 has a 6.4 times higher risk of developing insulin-dependent diabetes than individuals typed negative for D/DR4.

In some cases it has also been demonstrated that a disease is more severe in patients having the disease-associated antigen than in those who do not have that antigen. For example, multiple sclerosis progresses more rapidly in D/DR2-positive patients than in D/DR2-negative patients. Moreover, relapses in certain diseases are more common in patients positive for the disease-associated antigens. Plainly, then, HLA-DR typing has great diagnostic and prognostic value.

However, the use of such typing processes and products and, therefore, the attainment of the important advantages that they would provide in identifying acceptable transplant donors and recipients and disease-susceptible individuals, has been severely restricted because the present typing procedure is complex and time consuming and because there are not sufficient HLA-DR antigens available to provide a useful and economical source for such processes and products.

DISCLOSURE OF THE INVENTION

The present invention solves the problems referred to by providing DNA sequences coding for the DR-β-chains, the major polymorphic regions of the DR locus of the human lymphocyte antigen complex, and diagnostic typing processes and products related thereto.

By virtue of this invention, the DNA sequences encoding the HLA-DR light or β-chains are now for the first time made available for use in HLA-DR typing processes and products. Not only are the DNA sequences of this invention able to be produced economically and in large amount, their use in typing processes and products substantially simplifies and reduces the cost of the former HLA-DR antigen-based typing processes and products. For example, the DNA typing process of this invention is simple, can be performed with as little as 10–20 ml of blood and can easily be scaled-up to several thousand typings.

Finally, the DNA sequences of this invention permit the expression of those sequences in appropriate hosts and the production of the specific DR β-chain antigens encoded by them, uncontaminated by other HLA-DR factors, for use as diagnostic, preventive or therapeutic agents.

BRIEF DESCRIPTION OF THE DRAWINGS

FIG. 2 is a schematic outline of one embodiment of a cloning process of this invention.

FIG. 5A depicts the sequencing strategy of the cDNA sequence HLA-DR-β-A.

FIGS. 5B, 5C, 5D and 5E depict the nucleotide and amino acid sequences of the cDNA sequence HLA-DR-β-A.

FIGS. 6A, 6B, 6C and 6D depict a comparison of the amino acid sequence deduced from the cDNA sequence HLA-DR-β-A, the amino acid sequence determined by Kratzin for an Ia antigen β-chain isolated from a DR2 homozygous line and the amino acid sequence deduced from a cDNA clone isolated by Larhammar from a DR3, w6 cell line.

FIGS. 7A–7B depicts the nucleotide and amino acid sequences of cDNA sequence HLA-DR-β-B.

FIG. 8 is a Southern blot of DNA from four individuals (DR 7/7, 6/6, 3/6 and 1/1) typed using one embodiment of a typing process of this invention.

FIG. 9 depicts three regions of nucleotide sequence mismatch between the coding regions of cDNA clones HLA-DR-β-A and HLA-DR-β-B. In FIG. 9, the black circles designate the nucleotide mismatches and the boxes the 19-mers prepared from these sequences.

BEST MODE OF CARRYING OUT THE INVENTION

Figure 1:
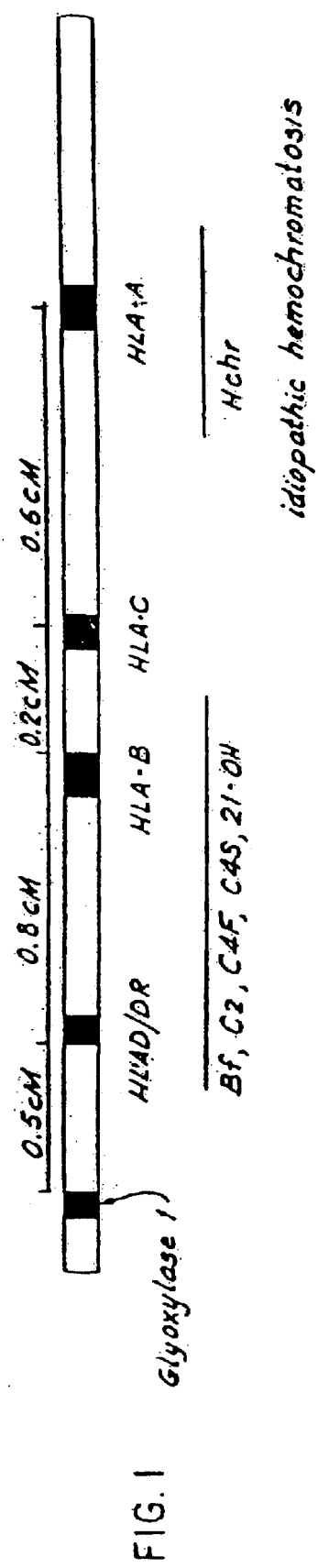
FIG. 1 is a schematic outline of chromosome 6 and the location of HLA loci on the short arm.

In order that the invention herein described may be more fully understood, the following detailed description is set forth.

In the description the following terms are employed:

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C and uracil ("U").

DNA Sequence—A linear array of nucleotides connected one to the other by phosphodiester bonds between the 3' and 5' carbons of adjacent pentoses.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode for the amino acid leucine ("Leu"), TAG, TAA and TGA are translation stop signals and ATG is a translation start signal.

Reading Frame—The grouping of codons during translation of mRNA into amino acid sequences. During translation the proper reading frame must be maintained. For example, the sequence GCTGGTTGTAAG may be translated in the three reading frames or phases, each of which affords a different amino acid sequence GCT GGT TGT AAG—Ala-Gly-Cys-Lys G CTG GTT GTA AG—Leu-Val-Val GC TGG TTG TAA G—Trp-Leu-(STOP)

Polypeptide—A linear array of amino acids connected one to the other by peptide bonds between the α-amino and carboxy groups of adjacent amino acids.

Genome—The entire DNA of a cell or a virus. It includes inter alia the genes coding for the polypeptides of the cell or virus, as well as its operator, promoter and ribosome binding and interaction sequences, including sequences such as the Shine-Dalgarno sequences.

Gene—A DNA sequence which encodes through its template or messenger RNA ("mRNA") a sequence of amino acids characteristic of a specific polypeptide.

Transcription—The process of producing mRNA from a gene or DNA sequence.

Translation—The process of producing a polypeptide from mRNA.

Expression—The process undergone by a DNA sequence or gene to produce a polypeptide. It is a combination of transcription and translation.

Plasmid—A non-chromosonal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance ($Tet^R$) transforms a cell previously sensitive to tetracycline into one which is resistant to it. A cell transformed by a plasmid is called a "transformant".

Phage or Bacteriophage—Bacterial virus, many of which consist of DNA sequences encapsidated in a protein envelope or coat ("capsid protein").

Cloning Vehicle—A plasmid, phage DNA or other DNA sequence which is able to replicate in a host cell, which is characterized by one or a small number of endonuclease recognition sites at which such DNA sequences may be cut in a determinable fashion without attendant loss of an essential biological function of the DNA, e.g., replication, production of coat proteins or lose of promoter or binding sites, and which contains a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes, which have been joined end-to-end outside of living cells and which have the capacity to infect some host cell and be maintained therein.

Expression Control Sequence—A sequence of nucleotides that controls and regulates expression of DNA sequences or genes when operatively linked to those sequences or genes. They include the lac system, the trp system, major operator and promoter regions of phage λ, the control region of fd coat protein and other sequences known to control the expression of genes of prokaryotic or eukaryotic cells or their viruses.

Referring now to FIG. 1, we have shown therein a simplified diagram of chromosome 6 and the location of HLA loci on the short arm of that chromosome. In view of the complexity of the HLA system, it was important to develop a mRNA translation assay that would distinguish between the various Ia-like antigens and the various HLA-DR antigens themselves.

Cell-free translation systems, like the rabbit reticulocyte lysate system, will not process or assemble multimeric proteins. On the other hand, *oocytes* of the clawed toad *Xenopus laevis* have been used as a translational system for a variety of proteins. Accordingly, we chose to investigate this latter system to assay for mRNA encoding the DR antigens. Using that system, we demonstrated that the three polypeptide chains of the HLA-DR antigens assemble in the *oocytes* and can be immunoprecipitated from them with anti-DR monoclonal antibodies. Therefore, this *oocyte* system provided to us an assay to select mRNA-encoding DR antigens.

Using mRNA-encoding DR antigen-rich fractions, identified in the above assay, we prepared cDNA from the mRNA, cloned it and selected and isolated clones containing the DNA sequences encoding the DR β-chain antigens of this invention. These DNA sequences were then employed in the processes and products of this invention to determine compatibility for tissue and organ transplants and to determine increased susceptibility of an individual to a wide variety of diseases. These DNA sequences are also useful in appropriate hosts to produce the antigens for which they encode, substantially uncontaminated by other HLA-DR factors, for use in diagnosis, therapy and the prevention of disease.

EXAMPLE

Preparation of HLA-DR Containing Poly A⁺ RNA

We grew a human β lymphoblastoid cell line, Raji cells, (a heterozygous cell line having two DR genes, DR3 and DR6) in RPMI 1640 medium, supplemented with 10% fetal calf serum, glutamine and gentamicin, substantially as described by S. Carrell et al., *Mol. Immunol*, 18, pp. 403–11 (1981). To provide a marker for following the products of the cells, we metabolically-labelled the cells by incubation for 16 h at 37° C. at a concentration of $2 \times 10^6$ cells/ml in complete methionine-free medium, supplemented with 1 mCi $^{35}$S-methionine per $50 \times 10^6$ cells. To produce unglycosylated DR molecules for our assays, we added tunicamycin at 2 μg/ml 2 h before the addition of the $^{35}$S-methionine.

We lysed the frozen cell pellets in ice-cold lysis buffer (10 mM Tris-HCl (pH 7.6), 0.1 M NaCl, 1% Nonidet P40) (1 ml buffer/$10^8$ cells) by vortexing four times for 15 sec, at 1 min intervals, and centrifuged the lysed cells (4° C., 4 min, 4000 rpm) in a Beckman J6 centrifuge (4500×g). We then loaded 4 ml of the cytoplasmic supernatant over the following gradient in an SW41 polyallomer tube: 2 ml CsCl (5.7 M) in 10 mM Tris-HCl (pH 7.4), 1 mM EDTA; 4.2 ml of a linear gradient of 40% to 20% (W/V) CsCl in 20 mM Tris-HCl (pH 7.4), 2 mM EDTA and 0.8 ml 5% (W/V) sucrose in 20 mM Tris-HCl (pH 7.4), 0.1 M NaCl, 4 mM EDTA. After equilibrating the gradients at 14° C., we pelleted the RNA (14° C., 14 h, 37000 rpm). For larger RNA preparations, we used SW27 tubes at 26000 rpm for 16 h at 14° C.

To recover the RNA from the tubes, we inverted the tubes and cut off the bottoms. We then dissolved the RNA in 10 mM Tris-HCl (pH 7.4), 1 mM EDTA, adjusted the mixture to 0.3 M sodium acetate (pH 5.0) and precipitated the RNA with 2 vol ethanol. We again dissolved the RNA in 10 mM Tris-HCl; (pH 7.4), 1 mM EDTA and 1% SDS, heated it at 100° C. for 2 min and cooled the mixture to room temperature. After addition of 1 vol 10 mM Tris-HCl (pH 7.4), 1 mM EDTA, 1 M NaCl, we loaded the RNA onto an obliga(dT) cellulose column (Collaborative Research) and eluted the poly A⁺ RNA fraction with H₂O and precipitated it twice with EtOH in the absence of EDTA (FIG. 2).

We size fractionated the poly A⁺ RNA on an agarose-urea gel, using a buffer system (6 M urea in 25 mM sodium citrate (pH 3.8)), substantially as described by Rosen et al., *Biochemistry* (Wash.), 14, pp. 69–78 (1975). (FIG. 2). This buffer system is well suited for high capacity and high resolution fractionation. It is also fully denaturing [H. Lehrach et al., *Biochemistry*, 16, pp. 4743–51 (1977)].

To carry out the poly A⁺ RNA fractionation we dissolved 500 μg poly A⁺ RNA in 100 μl 10 mM Tris-HCl (pH 7.4), 1 mM EDTA, 0.5% SDS, added 200 μl DMSO (99%) and adjusted the solution to 1 mM EDTA and pH 8.0. We then heated the solution at 45° C. for 5 min and loaded it on to a 4×0.5 cm slot (2.5% agarose gel). We electrophoresed the gel in the cold for 36 h, until the bromophenol blue reached the bottom of the gel. To prepare various size fractions (700–1600 nucleotides in length), we cut out 2 mm slices along the gel and dispersed the fractions with an Ultra-Turrax in 4 ml 10 mM Tris-HCl (pH 7.4), 10 mM EDTA, 0.5 M NaCl, 0.1 mg/ml *E. coli* tRNA. After adjusting the dispersed suspension to 0.5% SDS, we shook it overnight and then isolated the poly A⁺ RNA from the supernatant by chromatography over small oligo(dt)-cellulose columns and precipitated it twice with EtOH in the absence of EDTA. We monitored recovery by including 3' end-labelled Raji mRNA in the sample before the preparative gel electrophoresis.

To assay the HLA-DR activity (if any) of the various poly A⁺ RNA fractions, we translated the RNA in *oocytes* and immunoprecipitated the products with three monoclonal antibodies D1-12, D4-22 and BT 2.2.* In this assay we manually isolated stage 6 *oocytes* from *Xenopus laevis* ovaries after a 90–120 min incubation at room temperature with agitation in 0.2% crude collagenase (Sigma C-0130) in CA⁺⁺-free OR2 medium [Wallace et al., *J. Exp. Zool.*, 184, pp. 321–34 (1973)]. We then injected the *oocytes* with 20 ng poly A⁺ RNA in 50 nl, substantially as described by V. A. Moar, *J. Mol. Biol.*, 61, pp. 63–103 (1971) and incubated them for 24 h in OR2 medium containing 0.5 mCi/ml $^{35}$S-methionine and 50 units/ml penicillin and streptomycin. After incubation, we homogenized the *oocytes*, substantially as described by Rungger and Turler, *Proc. Natl. Acad. Sci. USA*, 75, pp. 6073–77 (1978), except that 1 ml of buffer was used per 50 *oocytes*.**

*These monoclonal antibodies and their activities have been previously reported [S. Carrel et al., *Mol. Immunol.*, 18, pp. 403–11 (1981) (D1-12, D4-22); R. S. Accolla et al., *Eur. J. Immunol.*, 12, pp. 166–69 (1982) (BT 2.2).]

**To prepare non-glycosylated products for assay studies, we incubated the *oocytes* in the presence of 5 μg/ml tunicamycin for 12 h, injected them with RNA (50 nl) containing 40 μg/ml tunicamycin and incubated them for 24 h in DR medium containing 5 μg/ml tunicamycin substantially as described by Colman et al., *Eur. J. Biochem.*, 113, pp. 339–48 (1981).

We then adjusted the supernatant from the *oocyte* homogenate to 2 ml with 0.15 N NaCl, 0.25% Nonidet P40 and loaded it over a 1 ml column of lentil lectin-Sepharose (Pharmacia). After washing the column extensively with that buffer, we eluted the glycosylated material with the same buffer, containing 0.1 M α-methyl mannoside (1.3% $^{35}$S-methionine counts were eluted in the bound fraction). In susequent cloning experiments we omitted the lentil column.

The glycosylated material from the lentil lectin column was then adjusted to pH 8.0 with Tris-HCl (pH 7.0) and to 1% Aprotenin (Sigma) and we added 20 ul PX63 ascites per ml. After incubation for more than 2 h in the cold and incubation for another 2 h in the presence of excess protein-A-Sepharose (Pharmacia), we added 20 μl per ml of a mixture of anti-DR monoclonal antibodies (D1-12, D4-22, BT 2.2) in the form of ascites fluid. This corresponds to 1 μl of ascites per injected *oocyte*. After incubation overnight at 4° C., we spun down the samples for 3 min (Eppendorf microfuge) and discarded the pellets. This centrifugation is important in avoiding high background in the assay due to aggregated material.

We then added Protein A-Sepharose to the supernatant and continued incubation for 4 h. The immunoprecipitates were collected by centrifugation (microfuge) and washed twice in about 400 μl 50 mM Tris-HCl (pH 7.4), 5 mM EDTA, 0.15 M NaCl, 1% Nonidet P40, 10 mM methionine, 1% Aprotein, three times with about 400 μl of the same buffer without Aprotenin and 0.15 M Nacl, but with 0.5 M NaCl, and twice in about 400 μl 10 mM Tris-HCl (pH 7.4), 1 mM EDTA, 0.15 M NaCl, 0.5% Nonidet P40.

We then dissolved the immunoprecipitates in 25 μl 0.5 M Tris-HCl (pH 8.8), 1 M sucrose, 5 mM EDTA, 0.01% bromophenol blue, 3% SDS and 8.3 mM dithiothreitol by heating at 100° C. for 3 min and loaded the solution onto a 12% polyacrylamide SDS gel. We ran the gel in two dimensions, with nonequilibrium pH gradient electrophoresis in the first dimension, substantially as described by P. Z. O'Farrell et al., *Cell*, 12, pp. 1133–42 (1977). We fixed the gels in 10% trichloroacetic acid, treated them with Enhance (New England Nuclear), washed them in 20% methanol and 3% glycerol and dried them. We exposed the dried gels to preflashed Kodak X-AR film with intensifying screens (Cawo) at −70° C.

Using this assay, we identified fraction 31, containing mRNA's 1200–1300 nucleotides long as the fraction containing RNA's coding for the α, intermediate and β-chains of HLA-DR. The RNA of this fraction was enriched about 20-fold over total poly A+ RNA.

Our assay of the size-fractionated RNA was based on a number of previous analyses of translated RNAs and DR antigens from Raji cells. From these analyses we had determined that the *oocytes* translated the RNA coding for the α, intermediate and β-chains of HLA-DR, glycosylated those antigens and assembled them. We had also determined that the assembly was immunoprecipitated by monoclonal antibodies D1-12, D4-22 and BT 2.2, but that only the β-chains were immunoprecipitated with BT 2.2, after the antigen assemblies were denatured. We had also determined that the α-chain had an apparent molecular weight of 35000–36000, the intermediate chain had about a 33000 apparent molecular weight and the β-chains had apparent molecular weights of 31000 and 29000 in the SDS-polyacrylamide gels. In addition, the non-glycosylated species appeared as follows: 30000 and 29000 (α-chain), 27000 (intermediate) and 27000 and 26000 (β-chains).

Construction of cDNA Clones

1. Preparation of HLA-DR cDNA

To prepare a single-stranded cDNA copy of the poly A+ RNA of Fraction 31, we denatured the RNA by adding $CH_3Hg$ to 5 mM and allowed the mixture to stand at room temperature for 1 min. We then added to the denatured RNA 1 ml/40 μg RNA of a buffer (50 mM Tris-HCl (pH 8.3), 10 mM $MgCl_2$, 70 mM KCl, 30 mM β-mercaptoethanol, 4 mM sodium pyrophosphate), 0.5 mM dGTP, dATP and dTTP, 0.3 mM α-$^{32}$P-dCTP (~0.5 μCi/nmole), 40 μg/ml oligo (dT) 12–18 (Collaborative Research) and 300 units/ml reverse transcriptase (Life Sciences, Inc.) and heated the mixture at 37° C. for 10 min and at 42° C. for 60 min [Wahli et al., *Dev. Biol.*, 67, pp. 371–83 (1978)] (FIG. 2).* We stopped the reaction by adding to this mixture EDTA to 10 mM and SDS to 0.1% and extracted the mixture with phenol/chloroform/isoamylalcohol (100:99:1). We washed the aqueous phase over a Sephadex G-50 superfine column in 10 mm Tris-HCl (pH 7.6), 1 mM EDTA. We then made the eluted mixture 0.5 N in NaOH, incubated it for 30 min at 37° C., neutralized it with 0.1 vol each of 5 M HOAc and 1 M Tris-HCl (pH 7.6) and ethanol precipitated the single-stranded cDNA. After collecting the cDNA by centrifugation, we resuspended it in 50 ul 0.5 N NaOH, incubated it for 30 min at 37° C. and layered it onto a 4 ml 5–20% alkaline sucrose gradient in 0.9 N NaCl, 0.1 M NaOH, 2 mM EDTA. We size fractionated the layered cDNA in an SW 60 rotor. (50000 rpm, 1° C., 7.5 h) and pooled the fractions containing cDNA having a length of more than 1000 nucleotides. We neutralized the pooled DNA and precipitated it as before (FIG. 2).

* The addition of the sodium pyrophosphate causes a precipitate which disappears when the reaction is stopped.

We prepared double-stranded cDNA from the above-pooled fractions by denaturing the cDNA by heating it at 68° C. for 90 sec and quick chilling it in ice. We then prepared the following reaction mixture: single stranded cDNA (40 μg/ml), 50 mM Tris-HCl (pH 8.3), 10 mM $MgCl_2$, 70 mM KCl, 30 mM β-mercaptoethanol, 0.5 mM of each dNTP and 300 units/ml reverse transcriptase and heated the mixture for 10 min at 37° C. and for 90 min at 42° C. We again stopped the reaction by the addition of EDTA to 10 mM and extracted it with phenol/chloroform/isoamylalcohol (100:99:1) and chromatographed it over a Sephadex G-50 column in 10 mM Tris-HCl (pH. 7.6), 1 mM EDTA.

We nicked the hairpin loop in our double-stranded cDNA preparation with $S_1$ nuclease in a reaction mixture containing 60 mM NaCl, 6 mM NaOAc (pH 4.8), 0.5 mM $ZnCl_2$, ~30 μg/ml double-stranded cDNA, 100 units/ml $S_1$ nuclease (P-L Biochemicals) by heating the mixture for 30 min at 37° C. We stopped the reaction by the addition of EDTA to 10 mm and Tris-HCl (pH 7.6) to 100 mM, extracted the mixture with phenol/chloroform/isoamylalcohol (100:99:1) and purified it by washing it through a Sepharose CL-GB column with 10 mM Tris-HCl (pH 7.6), 1 mM EDTA. We then precipitated the cDNA with EtOH as before.

2. Cloning of HLA-DR cDNA

A wide variety of host/cloning vehicle combinations may be employed in cloning double-stranded cDNA. In addition, within each specific cloning vehicle various sites may be selected for insertions of the double-stranded cDNA. It should be understood that the particular selection from among these various alternatives for cloning the DNA sequences of this invention may be made by one of skill in the art without departing from the scope of this invention.

For our initial cloning work, we chose the bacterial plasmid pBR322 (F. Bolivar et al., "Construction And Characterization Of New Cloning Vehicles II. A Multi-Purpose Cloning System", *Gene*, 2(2) pp. 95–114 (1977); J. G. Sutcliffe, "pBR322 Restriction Map Derived From The DNA Sequence: Accurate DNA Size Markers Up To 4361 Nucleotide Pairs Long", *Nucleic Acids Research*, 5, pp. 2721–28 (1978), the PstI site therein [L. Villa-Komaroff et al., "A Bacterial Clone Synthesizing Proinsulin", *Proc. Natl. Acad. Sci. USA*, 75, pp. 3727–31 (1978)], dC/dG tailing [L. Villa-Komaroff et al., supra] and *E. coli* HB101.

a. Preparation of PstI-cleaved, dG-tailed pBR322

We digested pBR322 with PstI using standard conditions. We then prepared a reaction mixture of 200 mM K-cacodylate, 50 mM Tris-HCl (pH 6.9), 10 mM $MgCl_2$, 1 mM dGTP, 200 μg/ml linearized pBR322 and 25 units/ml terminal transferase. After heating the mixture at 37° C. for 45 min, we stopped the reaction by adding EDTA to 10 mM and SDS to 0.5% and chilled the mixture in ice for 15 min and prepared the supernatant for annealing to dC-tailed HLA-DR cDNA by centrifugation (microfuge, 2 min, 4° C.) (FIG. 2).

b. Preparation of dC-tailed HLA-DR cDNA

We added dC tails to the cDNA, prepared above, in a reaction mixture containing 200 mM K-cacodylate, 50 mM Tris-HCl (pH 6.9), 1 mM dCTP, 100 μg/ml BSA (Pentex), ~2 μg/ml cDNA and 125 units/ml terminal deoxynucleotidyl transferase (P-L Biochemicals) by heating the mixture at 37° C. for between 1 and 6 min. We selected, the optimal reaction time (usually about 4 min) by using small aliquots. We then used that time to tail the cDNA. We again stopped the reaction by adding EDTA to 10 mM and SDS to 0.5% and by chilling the mixture in ice for 15 min. We isolated the dC-tailed cDNA for annealing to the dG-tailed Pst-cleaved pBR322 by centrifugation (microfuge, 2 min. 4° C.) (FIG. 2).

c. Annealing of dC-tailed cDNA and dG-tailed pBR322

We combined 40 ng of the dC-tailed cDNA prepared above and 250 ng of the dG-tailed, Pst-cleaved pBR322 prepared above in annealing buffer (10 mM Tris-HCl (pH 7.6), 1 mM EDTA, 0.2 M NaCl) at 68° C. for 2 h, followed by slow cooling (FIG. 2).

It should be understood that only a few of the recombinant DNA molecules prepared above will actually contain a DNA sequence coding for the β or light chains of HLA-DR, the chains encoding the major polymorphic region of the HLA-DR locus. In fact, the majority of the cloned species will be unrelated to HLA-DR or to the β-chains thereof.

3. Transfection of *E.coli* HB101 with Hybrids

We transformed competent *E. coli* HB101 (rec A⁻) with the above described hybrids substantially as described by D. Morrison, *J. Bacteriol.*, 132, pp. 349–51 (1977).

Since plasmid pBR322 includes the genes coding for ampicillin resistance and tetracycline resistance and since the former gene is inactivated by cDNA insertion at the PstI site, colonies that have been transformed with recombinant DNA molecules having cDNA inserts at the PstI site may be selected from colonies that have not been so transformed. Accordingly, we plated out *E. coli* cells transformed, as above, on washed and autoclaved Schleicher & Schuell nitrocellulose filters containing 10 µg/ml tetracycline [D. Hanahan and M. Meselson, *Gene*, 10, pp. 63–67 (1980)]. Using this procedure we prepared 550 cDNA clones (FIG. 2).

Screening for a Clone Containing HLA-DR cDNA

There are several approaches to screen a library of clones for a clone containing a particular recombinant DNA molecule, i.e, one containing an HLA-DR-β-chain related DNA insert. These methods are well known in the art. For our initial clone screening we chose to use high criteria positive hybridization selection to poly A⁺ RNA on diazobenzyloxymethyl paper (Schleicher & Schuell). Our protocol was modified from the procedure of Goldberg et al., *Methods Enzymol.* 68, pp. 206–20 (1979). As experimental basis for our hybridization, we had calculated that we should be able to detect one DR-β-cDNA-related clone in a pool of 50 colonies.

We divided 550 selected clones into 11 groups of 50 clones each and grew the pools in L-broth, supplemented with 10 µg/ml tetracycline. We then amplified the plasmids with chloramphenicol (50 µg/ml) overnight and prepared plasmid DNA from the pools using the conventional cleared lysate CsCl gradient procedure. We then treated the plasmid DNA with 0.5% diethylpyrocarbonate and passed it over a Sepharose B column (10 mM Tris-HCl (pH 7.6), 1 mM EDTA) to remove any contaminating small RNA molecules. We partially depurinated the plasmid DNA in 0.25 N HCl for 10 min at room temperature, adjusted the mixture to 0.5 N NaOH, 0.5 M NaCl incubated it for 20 min, neutralized it with HCl and precipitated the DNA twice with EtOH. We then prepared diazobenzyloxymethyl paper (Schleicher & Schuell) and covalently bound to it the above prepared DNA, substantially as described by Goldberg et al., supra. We monitored retention of the DNA by including a ³²P-labelled DNA tracer in the mixture. On average we bound 15 µg DNA to each 1 cm² filter.

We prehybridized the filters in 50% formamide (recrystallized twice and deionized), 20 mM PIPES (pH 6.4), 0.75 M NaCl, 2 mM EDTA, 0.4% SDS, 1% glycine, 0.3 mg/ml and *E. coli* tRNA, 0.1 mg/ml poly A at 37° C. for 2–4 h. For hybridization, we treated the eleven filters in ~200 ml of the same buffer without glycine, tRNA and poly A at 37° C. for 20 h with 300 µg total poly A⁺ RNA (prepared above). We then washed the filters three times with hybridization buffer at 37° C. for 30 min, three times at 22° C. for 30 min with 10 mM Tris-HCl (pH 7.4), 1 mM EDTA, 0.1 M NaCl, 0.1% SDS and three times at 50° C. for 10 min with 10 mM Tris-HCl (pH 7.4), 1 mM EDTA.

We eluted the hybridized RNA in two portions with 150 µl 5 mM Tris-HCl (pH 7.4), 0.5 mM EDTA, 6 µg/ml rabbit tRNA by heating the filter-containing solution at 98° C. for 75 sec. We then adjusted the mixture to 0.3 M NaOAc (pH 5.0) and precipitated the RNA twice with EtOH.

We complemented the RNA from above with mRNA for the HLA-DR α-chain and intermediate chain (selected from 25 µg poly A⁺ RNA under conditions of cDNA excess and confirmed by *oocyte* assay) and injected the complemented RNA into *oocytes* for assay as previously described. We complemented the RNA to increase the level of immunoprecipitation and to enhance our chances of finding a possible clone. In order to monitor the presence of any α-chain and intermediate chain antigens synthesized by *oocytes*, we immunoprecipitated one fourth of each *oocyte* extract with anti-DR rabbit serum 133 [Carrell et al., *Mol. Immunol.*, 18, pp. 403–411 (1981)] that binds free α-chains and intermediate chains. The remaining ¾ of each *oocyte* extract was immunoprecipitated with a pool of anti-DR-monoclonal antibodies (D1-12, D4-22, BT 2.2). In 2 of the 11 pools a small amount of DR-antigen (β) was synthesized in the injected *oocytes*.*

\* In some pools, an additional band of 37000 daltons was also immunoprecipitated. This protein was not identified.

We divided each of the two positive pools into 5 groups of 10 clones each an hybridized and assayed them as before. One out of the 5 groups derived from each of the original two positive pools was again positive. We then divided each of the positive groups into 10 groups of single clones each and hybridized and assayed them as before. We selected two positive clones: clone 68-6 and clone 83-7.

Clone 83-7 selected DR-β chain mRNA very efficiently under the conditions of hybridization. This mRNA produced in *oocytes* an antigen that was immunoprecipitated with the pool of anti-DR monoclonal antibodies (D1-12, D4-22, BT 2.2) in the absence of complementation with α and intermediate chain RNA. Conversely, clone 68-6 was much less efficient in selecting DR-β-chain mRNA. Clone 83-7 had an insert of 180 bp and clone 68-6 an insert of 470 bp. The inserts did not cross hybridize.

Figure 3:
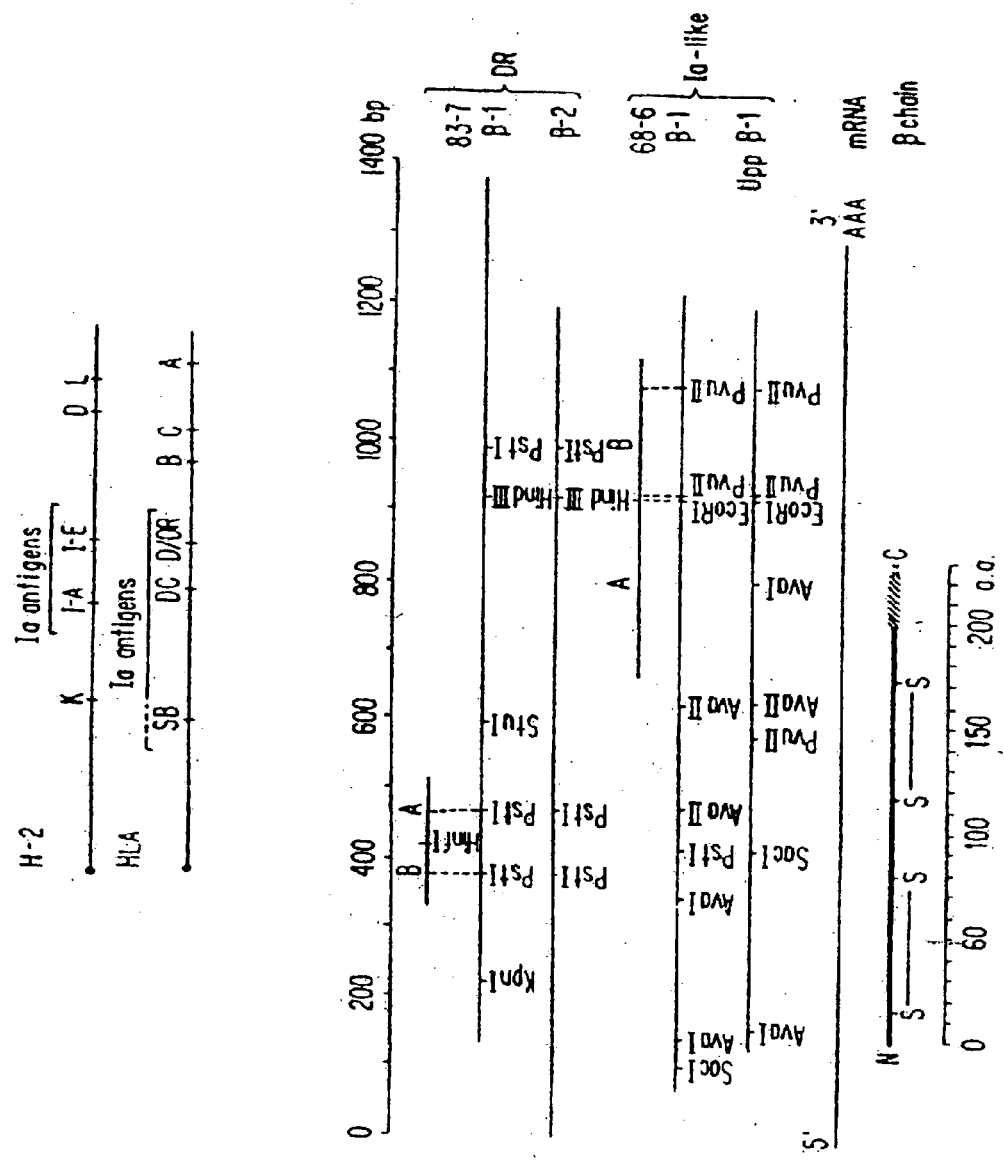
FIG. 3 is a partial restriction map of clones 83-7, 68-6, DR-β$_1$, DR-β$_2$ and Ia-β, of this invention. The restriction sites designated on this map are not exact. Conventional nucleotide sequencing would enable determination of the exact location of those sites.
Figure 6C:
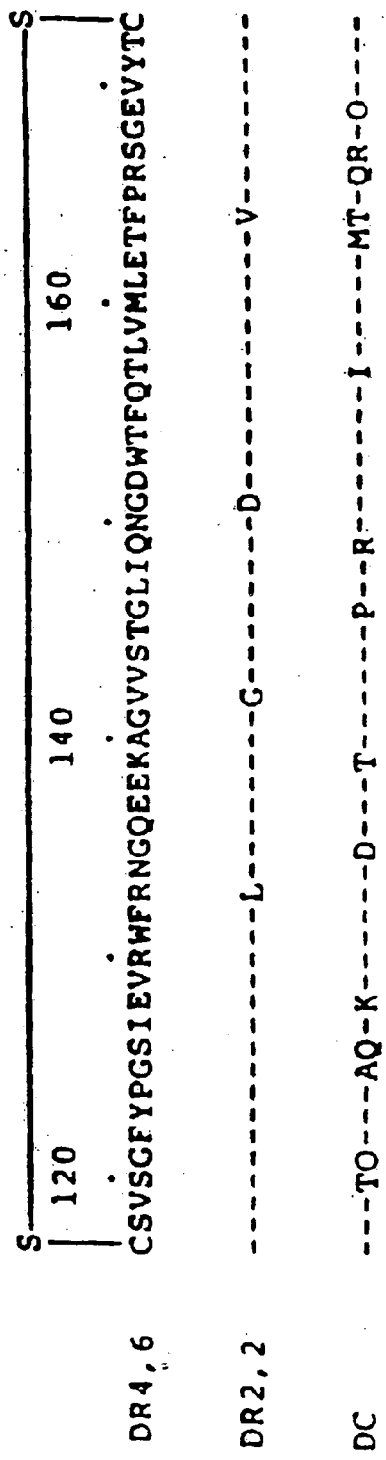

Referring now to FIG. 3, we have displayed therein the location of the cDNA insert of clone 83-7 in the DR domain and the location of the cDNA insert of clone 68-6 in the Ia-like domain. The Ia-like domain refers to a region of the HLA loci (FIG. 1). Clone 68-6 is designated Ia because it represents a region that is related to, but is not identical to, HLA/DR.

We also analyzed RNA homologous to these two cDNA clones by gel-transfer hybridization. Both cDNA clones hybridized with poly A⁺ RNA of about 1300 nucleotides in length, expressed in two B-cell lines and in B-cells from a patient with chronic lymphocytic leukemia, but absent in three T-cell lines, pancreas and liver. The 68-6 cDNA insert also hybridized to a minor RNA band 1650 nucleotides long, while the 83-7 cDNA insert hybridized to another RNA band 1900 nucleotides long.

Screening for Raji-Derived Clones Hybridizing to Clones 83-7 and 68-6

We employed the DNA inserts of clones 83-7 and 68-6 as probes to screen more extensive libraries of total poly A⁺ RNA-derived clones (Raji cells), prepared in substantially the same way as above, to locate other preferably longer and more complete DNA sequences from the HLA-DR β coding region.

We excised the inserts from the plasmid DNA of the two clones by PstI digestion and purified them by neutral sucrose gradient centrifugation and acrylamide gel electrophoresis. We passed the eluted fragments over DEAE columns and labelled the purified inserts, substantially as described by M. Grunstein and D. Hogness, "Colony Hybridization: A Method For The Isolation Of Cloned DNAs That Contain A Specific Gene", *Proc. Natl. Acad. Sci. USA*, 72, pp. 3961–65 (1975); Rigby et al., *J. Mol. Biol.*, 113, pp. 237–51 (1977), to $2 \times 10^8$ cpm/μg by nick translation with ($\alpha$-$^{32}$P) nucleotides and DNA polymerase I (Boehringer-Mannheim) [Rigby et al., supra]. We then used this probe to screen our libraries for longer hybridization-related cDNA clones using high criteria conditions (infra).

From this screening we isolated a number of clones containing longer cDNA inserts. The inserts of these clones were designated DR-$\beta_1$, DR-$\beta_2$ and Ia-$\beta_1$. The regions spanned by these inserts are depicted in FIG. 3. As depicted in FIG. 3, the DNA inserts DR-$\beta_1$ and DR-$\beta_2$ are related to the DR loci while Ia-$\beta_1$ is related to the less defined Ia region.

We also carried out cross hybridization experiments with various fragments of these clones at several hybridization criteria to determine the degree of homology between the different cDNA clones that we had selected. DNA sequences from the 3' untranslated portion of the cDNA clones did not cross-hybridize at a high criterium (5° C. below Tm), at an intermediate criterium (24° C. below Tm) or even at a low criterium (43° C. below Tm). Conversely, DNA sequences, at the 5' end of clones, encoding the first domain of Ia-like region, rather than the DR β-chain loci, did cross-hybridize at the intermediate criteria. Therefore DR-related DNA sequences do not cross-hybridize to Ia-related DNA sequences, but Ia-related sequences cross-hybridized to other Ia-related sequences.

Restriction Mapping of cDNA Inserts

We mapped the HLA-related inserts of our various cDNA clones by restriction analysis using single and double digestions with various restriction endonucleases. We employed the conditions and buffers recommended by the endonuclease suppliers (New England Biolabs, Bethesda Research Lab, Boehringer) and analyzed the resulting fragments on agarose gels.

Referring again to FIG. 3, we have depicted therein the partial restriction maps of various cDNA inserts located in our screening process. The actual location of the restriction sites depicted in FIG. 3, of course, is inexact. Nucleotide sequencing using conventional methods will properly locate the particular sites as well as other predicted sites.

As noted previously, Raji cells are heterozygous, i.e., DR 3/6. Therefore, the fact that two different sequences DR-$\beta_1$ and DR-$\beta_2$ were located in cDNA produced from those cells does not convincingly demonstrate that the two DNA sequences that characterize those clones originate from different families of β-chain coding sequences. Instead, the two may be allelic varients of the two DR types of the heterozygous cell line.

Screening for IBW 9 Derived Clones Hybridizing to Clone DR-$\beta_1$

We employed the DNA insert DR-$\beta_1$ as a hybridization probe to screen a library of 20,000 total poly A$^+$ RNA clones derived from a human β cell line, IBW 9. We prepared this library substantially as described for our Raji cell library. IBW 9 is a cell line that was originally thought to be homozygous for HLA by cosanguinity. It was, however, subsequently typed independently by two laboratories as a DR4, w6 heterozygous line.

We had employed what we thought was a homozygous cell line to avoid the aforementioned possibility of the difficulties in detecting any allelic polymorphism that may be present in heterozygous cell lines, like Raji cells. In contrast to heterozygous lines, β-chain clones detected in clones from homozygous cells lines will, by definition, represent different β-chain gene families. However, as noted above, the line employed by us was in fact heterozygous.

As a result of our screening of this heterozygous cell line-derived library, we located four families of HLA-DR-related DNA sequences. We designated these families of coding sequences DR-β-A, DR-β-B, DR-β-C and DR-β-D on the basis of restriction mapping.* It should, of course, be understood that other β-chain families may also exist. For example, Accolla, supra, has predicted 7 such families. Such families are part of this invention because they may be selected using the DR-$\beta_1$, DR-$\beta_2$, DR-β-A, DR-β-B, DR-β-C or DR-β-D sequences of this invention or fragments thereof in high criterium hybridization, substantially as described heretofore or using other similar procedures.

* The clones including those inserts are designated *E.coli* HB101 (pBR322(Pst)/HLA-DR-β-A through D) to connote that they are *E.coli* HB 101 cells that have been transformed with a recombinant DNA molecule comprising pBR322 which carries at its Pst I restriction site the particular HLA-DR-β related DNA insert.

Figure 4:
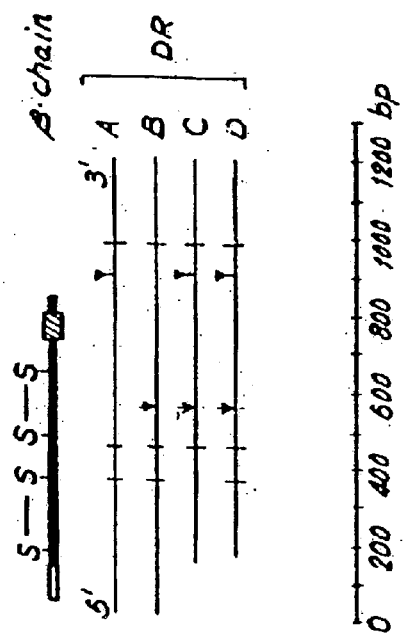
FIG. 4 depicts a partial restriction map of the cDNA sequences of HLA-DR-β-A, HLA-DR-β-B, HLA-DR-β-C and HLA-DR-β-D.

Clones in our four families of DR-β clones cross-hybridized well throughout their coding and non-coding regions. They may be distinguished by restriction mapping and also by cross-hybridization at very high stringencies (FIG. 4). Therefore, they most likely represent four mRNAs derived from four different DR-genes. Because they are derived from a cell line heterozygous for DR (4, w6), the four DR-β genes are believed to represent at least two non-allelic loci encoding DR-β chains. This conclusion is also supported by an analysis of genomic DNA clones that we isolated from the same β-cell line using our $\beta_1$ probe.

Nucleotide Sequencing of cDNA Inserts

For nucleotide sequencing, we prepared restriction fragments, as above, from the DNA inserts DR-β-A, DR-β-B, DR-β-C and DR-β-D, extracted them from acrylamide gels and purified them over DEAE-cellulose columns. We 3' labelled the fragments with ($\alpha$-$^{32}$P) cordyapin-5'-triphosphate (Amersham) and terminal deoxynucleotidyl transferase (P-L Biochemicals) or 5' labelled them with calf intestinal phosphatase (a gift of S. Clarkson) and polynucleotide kinase (P-L Biochemicals). We sequenced the labelled fragments substantially as described by Maxam and Gilbert, "A New Method For Sequencing DNA", *Proc. Natl. Sci. USA*, 74, pp. 520–64 (1977). Most stretches of cDNA were sequenced from both strands and most restriction sites which served as labelled termini were sequenced using fragments spanning them.

Referring now to FIGS. 5B, 5C, 5D and 5E, we have depicted therein the sequencing strategy and the nucleotide and amino acid sequences of the coding strand of cDNA clone HLA-DR-β-A.* In clone HLA-DR-β-A thirty-five nucleotides precede the first ATG triplet. This ATG is the first codon of an open reading frame 266 amino acids long. The first 29 amino acids, having a core of 11 consecutive hydrophobic residues, precede a sequence which has a high homology with partial amino acid sequences determined for the β-chain of human Ia antigens [D. A. Shackelford et al., *Immunol. Rev.*, 66, pp. 133–87 (1982)]. Therefore, the first 29 amino acids (numbered -1 to -29 in FIG. 5B) likely represent the signal sequence and the remaining 237 amino acids (numbered 1 to 237 in FIGS. 5B, 5C, 5D and 5E) represent the mature protein (199 amino acids), the transmembrane region (22 amino acids) and a cytoplasmic tail (16 amino acids). As depicted in FIGS. 5B, 5C and 5D, there are four cysteines in the extracellular portion of the coding sequence (positions 15, 79, 117 and 173).

* The partial nucleotide and amino acid sequence (AA79-95) for this clone was depicted in Great Britain patent applications 8222066 and 8230441.

Referring now to FIGS. 6A, 6B, 6C and 6D, we have depicted therein an amino acid sequence comparison of the amino acid sequence that we deduced from clone HLA-DR-β-A, the sequence determined by Kratzin for an Ia antigen β-chain isolated from a DR2 homozygous line [E. Kratzin et al., Hoppe Seyler's Z. Physiol. Chem., 362, pp. 1665–69 (1981)] and the sequence deduced from a cDNA clone isolated from a DR3, w6 cell line [D. Larhammar et al., Proc. Natl. Acad. Sci. USA, 79, pp. 3687–91 (1982)]. We believe this latter sequence is a DC β-chain clone because the deduced sequence matches the partial N-terminal sequence determined for the DS β-chain [S. M. Goyert et al., J. Exp. Med., 156, pp. 550–66(1982).*

* DS and DC antigens are identical and show very good homology with the mouse I-A Ia antigens [S. M. Goyert et al., J. Exp. Med., 156, pp. 550–66 (1982); R. Bono and J. L. Strominger, Nature, 299, pp. 836–38 (1982)].

Referring now to FIGS. 7A–7B we have depicted the nucleotide and amino acid sequences of another HLA-DR-β clone [HLA-DR-β-B]. Again, the amino acid sequence deduced from this clone has a 29 amino acid putative signal sequence and 237 other amino acids in the coding region.

Use of the cDNA Inserts of this Invention in HLA-DR Typing

The cDNA inserts coding for families of HLA-DR-β-chain antigens or fragments thereof may be used in DR typing processes and kits. In general such typing processes comprise the steps of (1) restricting an individual's DNA using conventional endonucleases and conditions, (2) size fractionating the restricted DNA, for example on conventional gels, (3) hybridizing the size fractionated DNA to the HLA/DR-β-chain related probes of this invention or fragments thereof and (4) detecting the areas of hybridization.

For example, as one illustration of such a process, we obtained high molecular weight DNA from four different individuals (3 homozygous (1/1, 6/6, 7/7) and 1 heterozygous (3/6) for HLA-DR) from established cell lines. We digested the DNA at 37° C. overnight with EcoRI (Boehringer-Mannheim), HindIII (Bethesda Research Laboratories) or BamHI using standard buffer conditions and 1 unit enzyme/μg DNA. We stopped the reactions with EDTA and extracted the restricted DNA once with chloroform/isoamylalcohol (24:1) and precipitated it with EtOH. After centrifugation, we resuspended the pellets in 10 mM Tris-HCl (pH 7.6), 1 mM EDTA, 0.1% SDS, 0.05% bromophenol blue, 0.05% xylene cyanol and 5% glycerol. After incubating the DNA for 4 h at 37° C., we treated it for 5 min at 65° C. and loaded it onto 0.6% agarose gels in 200 mM glycine, 15 mM NaOH (pH 8.3). We ran the gels at 60–100 V for 12 h, and treated and transferred them to 0.2μ nitrocellulose filters (Schleicher & Schull), substantially as described by G. M. Wahl et al., Proc. Natl. Acad. Sci. USA, 76, pp. 3683–87 (1979).

After transfer, we rinsed the filters in 4×SSC (SSC is 150 mM NaCl, 15 mM trisodium citrate) and then baked them for 2 h at 80° C. in a vacuum oven. We then incubated the filters successively in 5×SSC, 5× Denhardt's reagent for 1–2 h at 65° C. with gentle shaking and for 2 h at 65° C. in 1× Denhardt's reagent, 0.75 M NaCl, 5 mM EDTA, 50 mM sodium phosphate buffer (pH 7) 10% dextran sulfate, 0.1% SDS, 50 μg/ml poly G and 250 μg/ml sonicated denatured herring DNA. We then hybridized the filter-bound DNA for 8–12 h at 65° C. in 1× Denhardt's reagent, 0.75 M NaCl, 5 mM EDTA, 50 mM sodium phosphate buffer (pH 7), and 1×10$^6$ cpm/ml of a $^{32}$P-labelled cDNA probe of this invention.

After hybridization we washed the filters twice (65° C., 30 min) with each of 5×SSC, 1× Denhardt's reagent, 0.1% SDS, 0.1% sodium pyrophosphate; 2×SSC, 0.1% SDS; 0.5×SSC; and 0.1×SSC. We then exposed the dried filters to preflashed Kodak X-AR film with intensifying screens (Cawo) at −70° C. for 48 h.

Referring now to FIG. 8, we have displayed the results of the hybridization. As can be seen in FIG. 8, each different human DNA (DR 7/7 (lane 1), DR 6/6 (lane 2), DR 3/6 (lane 3) and DR 1/1 (lane 4)) exhibits a different electrophoretic pattern for each restriction endonuclease set.* Therefore, Southern blots of DNA from various HLA/DR typed individuals using the probes of this invention can distinguish among individuals of different HLA-DR specificities simply and economically.** Moreover, the simple blot patterns obtained in these typing processes and products may permit typing refinements, not possible in classical typing procedures, so as to identify and to distinguish various subgroups in conventional HLA-DR groups and better to determine the susceptibility of those subgroups to various diseases.

* Lane 5 of FIG. 8 is mouse DNA.
** The "typing" procedure described above may be done with 10–20 ml of blood and is easily scaled up to 100's or 1000's of tests.

It should of course be understood that the detection of the hybridizing portions of the restricted particular DNA need not be done by a $^{32}$P-labelled probe. Instead, other methods of detecting hybridization may be equally well employed. Such methods include coupling the probe to dye activators, detectable enzymes, avidin, or other detection means.

Improved HLA-DR Typing Using Synthetic Probes of the cDNA Inserts of this Invention Hybridization under conditions of Southern blotting with short (19 base) oligonucleotide DNA fragments has been shown to allow the discrimination of perfect matching sequences (identical or allele) from mismatching sequences (a different sequence or allele). See, e.g., B. J. Conner et al., Proc. Natl. Acad. Sci. USA, 80, pp. 278–282 (1983).

We have analyzed the nucleotide sequences of our HLA-DR-β-cDNAs and identified at least three regions within those sequences that display sequence differences (including polymorphic differences). These three regions are: (1) the coding sequence for amino acids 8–14; (2) the coding sequence for amino acids 26–32; and (3) the coding sequence for amino acids 72–78 (FIG. 9). We also identified a region (the coding sequence for amino acids 39–45) that is identical among the different DR-β chain genes, and also among the DC and SB β-chain genes.

We prepared synthetic oligonucleotide (19-mer) probes spanning the three regions of mismatch (black circles in FIG. 9). The blocked areas of FIG. 9 depict the particular 19-mers prepared for each of the three regions of the two HLA-DR-β cDNA clones. Because each of these 19-mers has more than one mismatch, an unambiguous distinction among HLA-DR sequences can be made with each probe. Moreover, a 19-mer may be prepared from the homologous region, described above, to act as a positive hybridization control.

In like manner, a collection of 19-mer DNA probes from regions of mismatch and identity among the other HLA-DR-β chain genes may be prepared. Each of the probes will then be specific for a given DR specificity. Hybridization with the collection of probes and controls would, accordingly, allow the rapid and accurate DR typing of large numbers of individuals.

Expression of the DNA Sequences of this Invention

The level of production of a protein is governed by two major factors: the number of copies of its gene within the cell and the efficiency with which those gene copies are transcribed and translated. Efficiency of transcription and translation (which together comprise expression) is in turn dependent upon nucleotide sequences, normally situated ahead of the desired coding sequence. These nucleotide sequences or expression control sequences define, inter alia, the location at which RNA polymerase interacts to initiate transcription (the promoter sequence) and at which ribosomes bind and interact with the mRNA (the product of transcription) to initiate translation. Not all such expression control sequences function with equal efficiency. It is thus of advantage to separate the specific coding sequences for a desired protein from their adjacent nucleotide sequences and to fuse them instead to other expression control sequences so as to favor higher levels of expression. This having been achieved, the newly-engineered DNA fragment may be inserted into a multicopy plasmid or a bacteriophage derivative in order to increase the number of gene copies within the cell and thereby further to improve the yield of expressed protein.

A wide variety of host-expression control sequence vector combinations may, therefore be employed in producing HLA-DR-β chain-like polypeptides in accordance with the processes of this invention by inserting the appropriate coding sequences therein. For example, useful vectors may consist of segments of chromosomal, non-chromosomal and synthetic DNA sequences, such as various known bacterial plasmids from E. coli including col El, pCR1, pBR322 and their derivatives, wider host range plasmids, e.g., RP4, phage DNA, e.g. the numerous derivatives of phage λ and vectors derived from combinations of the above, such as vectors that include a portion of pBR322, a portion of phage λ and a synthetic portion. Useful hosts may include bacterial hosts such as strains of E. coli e.g. E. coli K12 MC1061, E. coli EB101, E. coli X1776, E. coli X2282, E. coli MRC1 and strains of Pseudomonas, Bacillus subtilis, Bacillus stearothermophilus and other bacilli, yeasts and other fungi, animal or plant hosts such as animal (including human) or plant cells in culture or other hosts. Useful expression control sequences may include the operator, promoter and ribosome binding and interaction sequences of the lactose operon of E. coli ("the lac system"), the corresponding sequences of the tryptophan synthetase system of E. coli ("the trp system"), the major operator and promoter regions of phage λ ($O_L P_L$ and $O_R P'_R$), the control region of the phage fd coat protein, or other sequences which control or aid the expression of genes of prokaryotic or eukaryotic cells and their viruses or various combinations of them.

Of course, not all host-expression control sequence-vector combinations may be equally efficient with a particular HLA/DR coding sequence. However, as described in this invention and giving due consideration to biosafety, the sites available in the HLA-DR-β coding sequences of this invention for particular constructions, the size of the HLA-DR β-chain polypeptides to be expressed, the susceptibility of those polypeptides to proteolytic degradation by host cell enzymes, the possible contamination of those polypeptides by host cell proteins difficult to remove during purification, the expression characteristics of HLA-DR-β coding sequences, such as the structure of the DNA coding sequence and the location of the start and stop codons with respect to the expression control sequences and other factors recognized by those skilled in the art, an appropriate combination may be selected wherein the HLA/DR-β-chain coding sequences of this invention are operatively linked to an expression control sequence in a vector and there employed to transform a host such that culturing the host produces the polypeptide coded for by the inserted coding sequence.

There are also various methods known in the art for inserting a DNA sequence and expression control sequence into a vector. These include, for example, direct ligation, synthetic linkers, exonuclease and polymerase-linked repair reactions followed by ligation, or extension of the DNA strand with DNA polymerase and an appropriate single-stranded template followed by ligation. Again, those of skill in the art may select one or more of such methods to express the DNA sequences of this invention without departing from the scope hereof.

It should also be understood that the actual. HLA/DR-β-chain coding sequences expressed in a chosen host-expression control sequence-vector combination of this invention may result in products which are not identical to the authentic HLA-DR-β chain antigens. For example, the coding sequence expressed might code for HLA-DR-β chains plus a methionine or other amino acids unrelated to HLA-DR-β chains. The DNA sequence expressed might alternatively code for only a part or parts of HLA-DR-β chains alone or together with methionine or other amino acids. These constructions and products are encompassed by this invention. For example, a host transformed with a nucleotide sequence coding for a HLA-DR-β chain-like polypeptide might produce that compound alone or fused to other amino acids or it might secrete that product. All that is necessary is that the product, either after isolation from the fermentation culture or after conventional treatment such as cleavage, synthetic linking or other well-known processes displays an immunological or biological activity of the HLA-DR-β chain antigens.

The above-described HLA-DR polypeptides after purification or antibodies raised against them may be employed to type individuals in conventional HLA-DR typing processes or kits or may be employed in other diagnostic, preventive or therapeutic agents or processes.

Microorganisms and recombinant DNA molecules prepared by the processes of this invention are exemplified by cultures deposited in the American Type Culture Collection in 10801 University Blvd., Manasas, Va. 20110-2209 on Jul. 28, 1982, and identified as DR-β-A, DR-β-B and DR-β-C:

DR-β-A : E. coli HB101 (pBR322(Pst)/HLA-DR-β-A)
DR-β-B : E. coli HB101 (pBR322(Pst)/HLA-DR-β-B)
DR-β-C : E. coli HB101 (pBR322(Pst)/HLA-DR-β-C)

These cultures were assigned accession numbers ATCC 39164, 39163 and 39165, respectively.

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. An HLA-DR typing kit comprising a DNA sequence selected from the group consisting of:

(a) the HLA-DR-β region I nucleic acid sequence which encodes for amino acids LELLKSE of the HLA-DR locus;

(b) the HLA-DR-β region I nucleic acid sequence which encodes for amino acids LEQVKHE of the HLA-DR locus;

(c) the HLA-DR-β region II nucleic acid sequence which encodes for amino acids FLERHFH of the HLA-DR locus;

(d) the HLA-DR-β region II nucleic acid sequence which encodes for amino acids FLDRYFY of the HLA-DR locus;

(e) the HLA-DR-β region III nucleic acid sequence which encodes for amino acids RGQVDNY of the HLA-DR locus;
(f) the HLA-DR-β region III nucleic acid sequence which encodes for amino acids RAAVDTY of the HLA-DR locus;
(g) DNA sequences which are fully complementary to any of the foregoing DNA sequences.

2. The typing kit of claim 1, further comprising a hybridization control of the formula GCTTCGACAGCGACGTGGG.

3. An HLA-DR typing process comprising the steps of:
(a) hybridizing DNA in a sample to be tested to a DNA sequence selected from the group consisting of:
  (i) the sequence which encodes for amino acids LELLKSE of the HLA-DR locus;
  (ii) the sequence which encodes for amino acids LEQVKHE of the HLA-DR locus;
  (iii) the sequence which encodes for amino acids FLERHFH of the HLA-DR locus;
  (iv) the sequence which encodes for amino acids FLDRYFY of the HLA-DR locus;
  (v) the sequence which encodes for amino acids RGQVDNY of the HLA-DR locus;
  (vi) the sequence which encodes for amino acids RAAVDTY of the HLA-DR locust;
  (vii) DNA sequences which are fully complementary to any of the foregoing DNA sequences, and
(b) detecting the hybridization between said sample DNA and said DNA sequence.

4. The HLA-DR typing process according to claim 3, further comprising the step of:
(c) comparing said hybridization to hybridization between DNA of known HLA-DR type and said DNA sequence.

5. The typing process of claim 3 or 4, wherein prior to the step of detecting the hybridization between the sample DNA and said DNA sequence, the process further comprises the step of hybridizing the sample DNA to a hybridization control of the formula GCTTCGACAGCGACGTGGG.

* * * * *

UNITED STATES PATENT AND TRADEMARK OFFICE
CERTIFICATE OF CORRECTION

PATENT NO. : 6,818,393 B1
DATED : November 16, 2004
INVENTOR(S) : Bernard F. Mach et al.

It is certified that error appears in the above-identified patent and that said Letters Patent is hereby corrected as shown below:

<u>Title page,</u>
Item [73], Assignee, replace "bioMirieux sa" with -- bioMérieux S.A. --.

Signed and Sealed this

Twenty-first Day of June, 2005

JON W. DUDAS
*Director of the United States Patent and Trademark Office*